(12) United States Patent
Tseng

(10) Patent No.: US 10,525,274 B2
(45) Date of Patent: Jan. 7, 2020

(54) CONNECTOR FOR DEPLOYING AN ENERGY TRANSMISSION MEDIUM, IN PARTICULAR OPTICAL FIBER

(71) Applicant: Hsiao Sen Tseng, Taichung (TW)

(72) Inventor: Hsiao Sen Tseng, Taichung (TW)

( * ) Notice: Subject to any disclaimer, the term of this patent is extended or adjusted under 35 U.S.C. 154(b) by 296 days.

(21) Appl. No.: 15/591,572

(22) Filed: May 10, 2017

(65) Prior Publication Data

US 2018/0207440 A1 Jul. 26, 2018

(30) Foreign Application Priority Data

Jan. 25, 2017 (TW) .............................. 106102930 A

(51) Int. Cl.
  *A61N 5/06* (2006.01)
  *A61M 5/158* (2006.01)
  *A61B 18/22* (2006.01)
  *A61B 18/24* (2006.01)
  *A61B 18/00* (2006.01)

(52) U.S. Cl.
  CPC ............ *A61N 5/0601* (2013.01); *A61B 18/22* (2013.01); *A61B 18/245* (2013.01); *A61B 2018/00345* (2013.01); *A61M 5/158* (2013.01); *A61N 2005/063* (2013.01); *A61N 2005/0612* (2013.01)

(58) Field of Classification Search
  USPC ......................................................... 606/14
  See application file for complete search history.

(56) References Cited

U.S. PATENT DOCUMENTS

| | | | | |
|---|---|---|---|---|
| 2002/0055716 A1* | 5/2002 | Nakagami | ......... | A61M 25/0631 604/164.12 |
| 2003/0236517 A1* | 12/2003 | Appling | ................. | A61B 18/24 606/7 |
| 2007/0005019 A1* | 1/2007 | Okishige | ............ | A61B 17/3478 604/175 |
| 2008/0249517 A1* | 10/2008 | Svanberg | ............. | A61N 5/0601 606/15 |
| 2008/0319387 A1* | 12/2008 | Amisar | .............. | A61M 25/0111 604/95.04 |
| 2011/0021911 A1* | 1/2011 | Waters | ................. | A61B 8/0883 600/439 |
| 2011/0263953 A1* | 10/2011 | Markle | ............. | A61B 5/14532 600/310 |
| 2018/0008803 A1* | 1/2018 | Muramatsu | ........... | A61M 5/158 |

* cited by examiner

*Primary Examiner* — Gary Jackson
*Assistant Examiner* — Zahed Kabir
(74) *Attorney, Agent, or Firm* — Muncy, Geissler, Olds & Lowe, P.C.

(57) ABSTRACT

The present invention discloses a connector for deploying an energy transmission medium, comprising a cylindrical tube and a telescopic arrangement comprising a fixed tube attached to and penetrating a sealed first end of the cylindrical tube, leaving a tunnel connecting an inner space of the cylindrical tube and the environment, and a sliding tube slidably engaged with the fixed tube and affixed with at least one energy transmission medium having a front end extending through out of the sliding tube towards a second end of the cylindrical tube and a tail end connected to an energy source coupler.

19 Claims, 5 Drawing Sheets

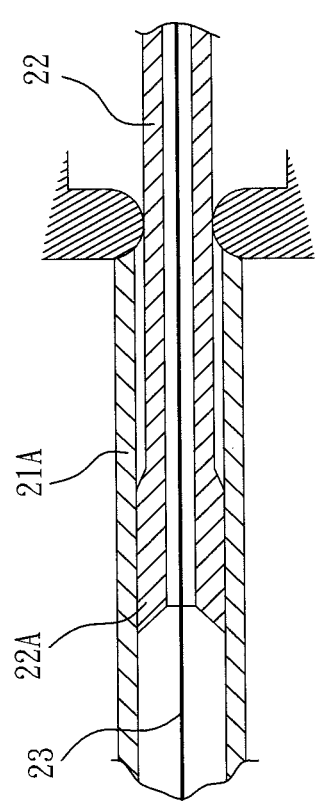
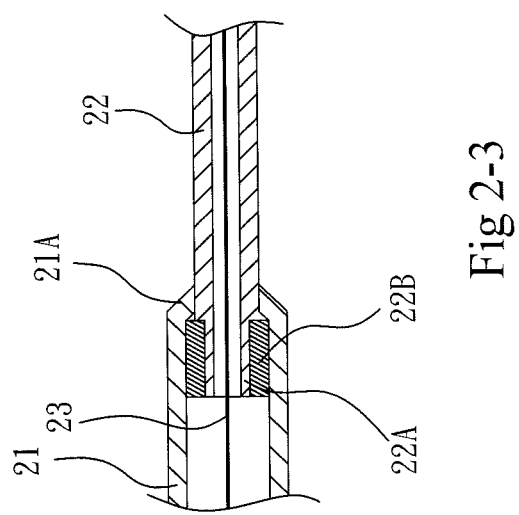
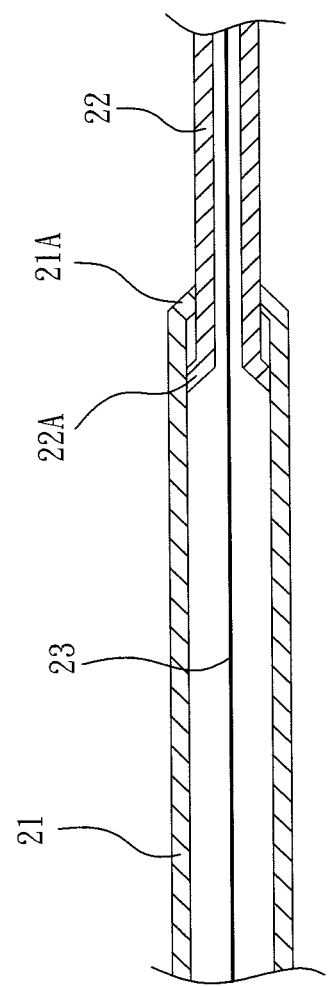
Fig 2-1
Fig 2-2
Fig 2-3

CONNECTOR FOR DEPLOYING AN ENERGY TRANSMISSION MEDIUM, IN PARTICULAR OPTICAL FIBER

CROSS REFERENCE TO RELATED APPLICATIONS

This non-provisional application claims priority benefit from Taiwan patent application filing number 106102930, filed on Jan. 25, 2017, the disclosure of which is incorporated herein by reference in its entirety.

FIELD OF INVENTION

The present invention relates to a connector for deploying an energy transmission medium, in particular optical fiber. The present invention provides an alignment mechanism with a simplified structure, to deploy an energy transmission medium into a thin tube.

PRIOR ART

In many applications it is necessary to introduce energy into an object using a transmission medium. The transmission medium may be a metal tube or a metal line for transmission of electricity or an optical fiber for transmission of light. One of the most popular applications is known as "acupuncture," wherein a metal needle is used to transmit electric power to a specific location in the human body.

In recent years, the application of introducing optical energy into a living organism, in particular into a blood vessel, a passage for body fluid, or an extracorporeal body fluid circulation circuit, in order to improve the health of living organism, has attracted the attention of the medical and healthcare communities.

When the optical energy is transmitted using a single optical fiber, the outer diameter of the optical fiber would fall within the range from 125 um to 500 um. The front end of the optical fiber would reach a depth of about 40 mm or more in the human body. Under this aspect ratio of outer diameter to length, an optical fiber or other transmission medium per se can't be implanted into the human body or other animal tissue to the desired depth, without any auxiliary device.

A possible solution to this issue would be to implant a rigid or flexible medical indwelling needle, such as an intravenous cannula or catheter, before the deployment of the optical fiber. The indwelling needle is pre-inserted into a tissue, a container or a conduit, such that the needle tip reaches a desired position, then the transmission medium is introduced into the lumen space of the needle shaft. Advance the transmission medium through the lumen until the front end of the transmission medium reaches or is adjacent to the desired position. In application, the tail end of the transmission medium is connected to an energy source. By turning on the power of energy source, the energy generated is transmitted to the front end through the transmission medium, and fanned out to the desired tissue or its adjacent space.

While the auxiliary device described above provides suitable conduit for energy delivery, the transmission medium would occupy all or most lumen space of the indwelling conduit. Taking the 22G indwelling cannula as an example. The internal diameter of an indwelling cannula is about 550 um, while the outer diameter of a commonly used transmission medium, such as a plastic optical fiber, is about 400-500 um. In this situation, when energy is delivered via an optical fiber, there is no space spare for the infusion therapy with medications or fluids by using the same indwelling conduit of needle or catheter. Thus, it is inconvenient to swap and exchange the optical fiber with the infusion therapy tube, before and after the energy transmission. Furthermore, repeatedly manipulating the optical fiber might also result in unexpected contaminations.

In fact, from the application point of view, a narrowed diameter of the transmission medium does not impact the energy transmission. Therefore, shrinking the diameter of the transmission medium to a quarter of its original, for example, 125 um, its cross-sectional area would occupy only $1/16$ or less of the lumen of indwelling conduit. There would be an ample space spare for the smooth infusion of injection fluids.

However, due to the narrowed diameter, the transmission medium becomes pliably thin. In this instance, aligning to advance the transmission medium into the lumen of the indwelling needle or catheter would be disturbing, because the thin pliable transmission medium tends to kink or prolapse during manipulation. Besides, viscous blood or body fluids might deposit in the lumen of indwelling conduit, which hinders not only the advancing but also the visual aiming of the transmission medium into the thin conduit.

It is thus necessary to provide a device that enables both the infusion of injection fluids and the transfer of energy simultaneously, using the same indwelling needle or catheter, without swapping the infusion tube or the energy transmission medium. It is also necessary to provide a device to assist the deployment of a pliably thin transmission medium.

SUMMARY OF THE INVENTION

The objective of this invention is to provide a connector for deploying an energy transmission medium, in particular optical fiber, into a tunnel, through which infusion of injection fluids and transfer of energy may be carried out simultaneously, without the need of swapping the infusion pipe or the energy transmission medium.

Another objective of this invention is to provide a connector for easy deployment of an energy transmission medium, wherein the connector has a simplified structure and enables the deployment of a pliably thin transmission medium into an indwelling needle or a catheter with relatively small inner diameter.

According to the present invention, a connector for deploying an energy transmission medium is provided. The invented connector assists the accurate implantation of a pliably thin transmission media into an indwelling needle or a catheter with relatively small inner diameter. After the transmission medium enters the lumen of the indwelling needle or the catheter, the lumen space remained ample for fluids to flow.

According to a preferred embodiment of the present invention, the connector for deploying energy transmission medium comprises: a cylindrical tube comprising a first end and a second end and a telescopic arrangement comprising a fixed tube attached to and penetrating the sealed first end of the cylindrical tube, preferably at a center of the first end, extending along a longitudinal direction of the cylindrical tube and having a maximum outer diameter smaller than an inner diameter of the cylindrical tube, leaving a tunnel connecting an inner space of the cylindrical tube and the outer environment, and a sliding tube slidably engaged with the fixed tube and comprising a first end and a second end; wherein at least one energy transmission medium is affixed to the sliding tube, with a front end of the transmission medium extending through out of the sliding tube towards the second end of the cylindrical tube and a tail end connected to an energy source coupler at a position immediate following the first end of the sliding tube or a position following an axial extension from the first end, to connect the transmission medium to an energy source. The transmission medium can be at least one optical fiber and/or at least one metal wire. In the preferred embodiments of the invention, the front end of the transmission medium extends to the second end of the fixed tube. An annual lock may encircle the first end of the sliding tube. The lock may be a male Luer plug.

In some preferred embodiments, the cylindrical tube further comprises a branch, with an internal space of the branch being in connection with the internal space of the cylindrical tube. The branch tube may form an angle with the main body of the cylindrical tube at their joint.

In many embodiments of the present invention, the telescopic arrangement comprises linear sleeve tubes, while in other embodiments, the telescopic arrangement comprises arc sleeve tubes. While the telescopic arrangement usually comprises two segments of tube, it may comprise more than two segments.

In the preferred embodiment of the invention, a tube having the largest outer diameter among the telescopic tubes extends to a position adjacent to the open second end of the cylindrical tube. In particular embodiments, the tube having the largest outer diameter extends beyond the open second end of the cylindrical tube.

In some embodiments of the invention, the open second end of the cylindrical tube has a reduced diameter and is configured to be coupled in a hub of an indwelling needle or a catheter, while in other embodiments, the second end is configured to embed a hub of an indwelling needle or a catheter.

A flexible tube bag may be provided to connect the coupler of the sliding tube to the first end of the cylindrical tube, to enclose the space between the coupler and the first end of the cylindrical tube.

In particular embodiments of the invention, a fixer is provided in at least one of the fixed tube and the sliding tube, to temporarily fix the relative positions of the two tubes, after they are engaged. In some embodiments of the invention, a stopper is provided in at least one of the fixed tube and the sliding tube to prevent the two tubes from separation, when the telescopic arrangement is fully extended or fully retracted after both tubes engaged.

The aforementioned and additional objectives and advantages of this invention may be clearly understood from the detailed description by referring to the following drawings.

SCHEMATIC SIMPLE EXPLANATION

FIG. 1 shows the structural schematics of one embodiment of the connector for deploying an energy transmission medium, in particular optical fiber of this invention.

FIGS. 2-1 to 2-3 respectively show the preferred embodiments of a fixer/stopper used in the telescopic arrangement according to the present invention.

EMBODIMENT

In the followings, the connector for deploying an energy transmission medium, in particular optical fiber of the present invention will be described by using its several embodiments. It shall be appreciated that description of the embodiments serves merely to illustrate the basic structure and spirit of the present invention. They shall not be used to limit the scope of protection of this invention.

Figure 1:
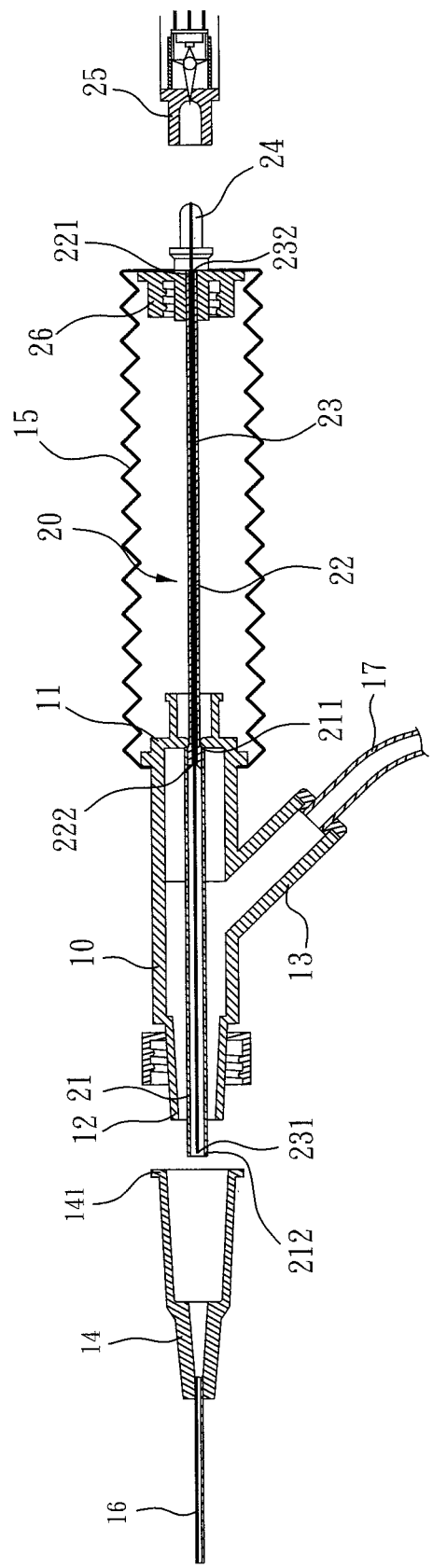

FIG. 1 shows the structural schematics of one embodiment of the connector for deploying an energy transmission medium, in particular optical fiber of this invention. As shown in this figure, the invented connector for deploying an energy transmission medium basically comprises two parts; they are a cylindrical tube 10 and a telescopic arrangement 20.

The cylindrical tube 10 shown in FIG. 1 forms a substantial cylinder. The cylinder 10 has a first end 11 and a second end 12, with the first end 11 being sealed. The second end 12 may be an open end. The cylindrical tube 10 shown in this figure has a branch or branch tube 13. The branch 13 is connected to the main body of the cylindrical tube 10, such that the internal space is in connection with the internal space of the cylindrical tube 10. The branch 13 is an element useful in the connector for deploying an energy transmission medium but it is not a compulsory element. The branch 13 forms an angle with the main body of the cylindrical tube 10 at their joint, which angle may be rectangular or acute, whereby the connector forms a T shape or a Y shape connector. The main function of the branch 13 is to allow fluids to access the internal space of the cylindrical tube 10 via the branch 13, whereby the fluids reaches or flows through the opening of the second end 12 of the cylindrical tube 10.

The telescopic arrangement 20 comprises a fixed tube 21 and a sliding tube 22 slidably engaged. To be specific, in the fixed tube 21 and the sliding tube 22, a tube having a larger outer diameter has an inner diameter that is substantially the same as the outer diameter of the other tube that has a smaller diameter. When the two tubes are engaged by inserting the narrow tube into the wide tube, the two tubes slide relatively, whereby the length of the telescopic arrangement 20 varies with its extension and retraction. While the inner and outer diameters of the two tubes fit each other, the inner space of the tubes is isolated or substantially isolated from the environment.

In the example shown in the figure, the fixed tube 21 is the wide tube and is fixed at the sealed first end 11 of the cylindrical tube 10. The fixed tube 21 further penetrates the first end 11, thereby connects the inner space of the cylindrical tube 10 to the environment. The fixed tube 21 is preferably deposited at the substantial center of the first end 11 of the cylindrical tube 10. The location of deposition, however, is not any technical limitation. The sliding tube 22 is the narrow tube and fits into the fixed tube 21, with the ability of sliding in the fixed tube 21 to realize the extension and contraction of the telescopic arrangement 20. However, the combination of the telescopic tubes and their length are not any technical limitation. For example, it is also possible to design such that the second end 222 of the sliding tube 22 extends to reach the second end 212 of the fixed tube 21, when the telescopic arrangement 20 is fully extended. In addition, it is also possible to specify the fixed tube 21 as the narrow tube and the sliding tube 22 the wide tube. Nevertheless, the telescopic arrangement 20 may include more than 2 segments, such as they may include 3 or more segments. Furthermore, the cross section of the telescopic arrangement 20 may be other than round shape; it can be rectangular, ellipse etc., as long as a narrow tube and a wide tube can slide relatively. The shape of the telescopic arrangement 20 after full extension is not necessary linear. It may be for example an arc or in another suitable shape. For the smooth flow of fluids in the inner cavity of the cylindrical tube 10, it is preferable that the maximum outer diameter of the telescopic arrangement 20 is less, preferably far less than the inner diameter of the cylindrical tube 10.

In the example of FIG. 1, the fixed tube 21 has a first end 211 and a second end 212 and extends along the longitudinal direction of the cylindrical tube 10, with the first end 211 fixed at the substantial center of the edge surface at the first end 11 of the cylindrical tube 10. In addition, in this example the second end 212 of the fixed tube 21 extends to reach the opening of the second end 12 of the cylindrical tube 10, while in another embodiment the second end 212 of the fixed tube 21 extends beyond the opening of the second end 12 of the cylindrical tube 10, to provide particularly excellent alignment capability. If necessary, a support may be formed to support the second end 212 of the fixed tube 21 eccentrically at the wall of the second end 12 of the cylindrical tube 10. In doing this, the support shall be specially designed, in order not to hinder liquids from flowing to the second end 12 via the branch 13 and the inner cavity of the cylindrical tube 10.

Preferably at least one position lock is formed in the fixed tube 21 and the sliding tube 22, to fix the relative positions between them when engaged. In addition, at least one stopper may be provided in the fixed tube 21 and the sliding tube 22, to prevent them from separation, when the telescopic arrangement 20 is fully extended or fully retracted when engaged. The stopper may nevertheless be the lock. FIG. 2-1 and FIG. 2-2 show two examples of the lock/stopper. In the example of FIG. 2-1 the wall of an end 21A of the fixed tube 21 has an increasing thickness along the longitudinal direction, whereby its inner diameter decreases along the longitudinal direction. At the same time, the wall of a corresponding end 22A of the sliding tube 22 has an increasing thickness along the longitudinal direction, whereby its outer diameter increases along the longitudinal direction. When the end 22A of the sliding tube 22 reaches its corresponding end 21A of the fixed tube 21, the sliding tube 22 is locked at that position, due to friction forces. The increased thickness of the tube walls also prevents the two sleeve tubes from separation when the telescope arrangement 20 is fully extended.

In the example of FIG. 2-2, an end 21A of the fixed tube 21 has a decreasing diameter, while a corresponding end 22A of the sliding tube 22 has an increasing diameter, whereby when the end 22A of the sliding tube 22 reaches its corresponding end 21A of the fixed tube 21, the sliding of the sliding tube 22 is stopped. This design, however, does not fix the relative positions of the two sleeve tubes.

Figure 3:
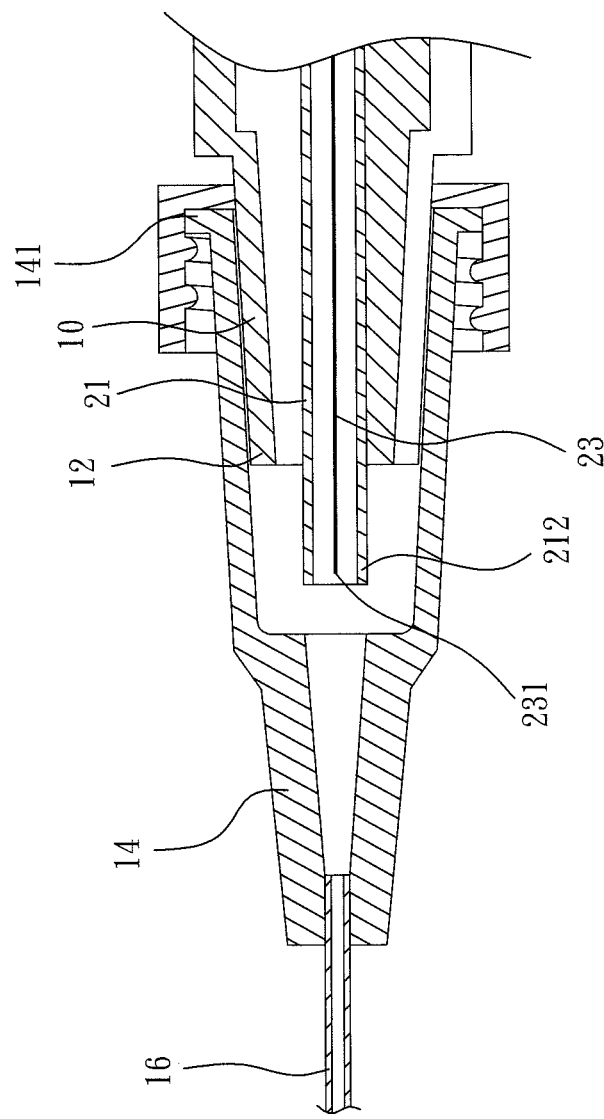
FIG. 3 shows the connector for deploying an energy transmission medium of this invention in an engaged/standby status.

FIG. 2-3 shows a further example, wherein an end 21A of the fixed tube 21 has a decreasing diameter, while on a corresponding end 22A of the sliding tube 22 a compressible lock/stopper ring 22B is fitted thereon, whereby the end 22A has an enlarged outer diameter. When the end 22A of the sliding tube 22 reaches its corresponding end 21A of the fixed tube 21, the sliding tube 22 stops moving and is locked at that position due to the compressive reaction force of the ring 22B.

A transmission medium 23 is affixed in the inner cavity of the sliding tube 22. The transmission medium 23 is the object to be deployed by using the invented connector. The transmission medium of 23 is generally an energy transfer medium, such as one or more optical fibers or metal wires, or a combination thereof. In case of a metal wire, the transmission medium may be coated with a dielectric layer on its surface. The transmission medium 23 may further comprise a supporting material or a protective material, such as glass fiber, a polymer, metal wire, metal coating and so on. The front end 231 of the transmission medium 23 extends beyond the second end 222 of the sliding tube 22, towards the edge of the second end 12 of the cylindrical tube 10. In the preferred embodiment of the invention, the front end 231 of the transmission medium 23 extends further to the edge of the second end 212 of the fixed tube 21. However, those having ordinary skills in the art would appreciate, length of the extension of the front end 231 of the transmission medium 23 in the fixed tube 21 shall depend on the desired depth of insertion of the transmission medium 23 in the living organism or passage.

In general, the transmission medium 23 may be affixed to the sliding tube 22 with its tail end 232. That is, at the first end 221 of the sliding tube 22 that is not yet inserted in the fixed tube 21, so that the transmission medium 23 can move along with the sliding of the sliding tube 22. However, it is also possible to fix the transmission medium 23 against the inner surface of the sliding tube 22 in its full length or a partial length thereof. In practical applications, the tail end 232 of the transmission medium 23 may further extend beyond the first end 221 of the sliding tube 22 and enter into a coupler 24, whereby the transmission medium 23 is affixed. If the transmission medium 23 is an optical fiber, the coupler 24 may be an optical fiber connector for the tail optical fiber, to couple with an energy source 25. In such applications, the first end 221 of the sliding tube 22 may first be encircled by an annular lock 26, which may be a male Luer plug, then the annular lock 26 is jointed to the coupler 24. The transmission medium 23 is affixed both in the coupler 24 and in the first end 221 of the sliding tube 22. The transmission medium 23 may be affixed in the sliding tube 22 by attaching it against the inner walls of the tube 22, along the central axis of the tube 22, or affixed in the sliding tube 22 by burying it in the inner walls of the tube 22 in its full length or a part thereof. The length of the fixation is not limited. For example, the transmission medium 23 may be affixed to the sliding tube 22 throughout the full length of the sliding tube 22.

FIG. 1 also shows a tapered outer diameter at the second end 12 of the cylindrical tube 10. The tapered structure so formed is used to be coupled to the hub of a male Luer slip connector, an indwelling needle 14, or a catheter. In some other embodiments of this invention, the second end 12 is configured as a male Luer lock connector, to couple with an indwelling needle 14 or a catheter. Under such a design, the connector for deploying a transmission medium serves to align the front end 231 of the transmission medium 23 to the entrance opening of the indwelling needle 14 or the catheter, and then to stably deploy the front end 231 of the transmission medium 23 into the lumen of the indwelling needle 14 or the catheter.

A flexible tube bag 15 may be disposed between the first end 221 of the sliding tube 22 and the first end 11 of the cylindrical tube 10, to enclose the space between the first end 221 of the sliding tube 22 and the first end 11 of the cylindrical tube 10. The flexible tube bag 15 may be any conventional tube bag, such as a pliable bag tube or a retractable bellow tube. In the preferred embodiment of the invention, the flexible tube bag 15 extends from the edge of the first end 221 of the sliding tube to the edge of the first end 11 of the cylindrical tube 10. The flexible tube bag 15 may enclose the exposed portion of the telescopic arrangement 20 either in the standby status or the deployment completed status, to protect the telescopic arrangement 20 and the transmission medium 23 therein from contamination. As a result, the transmission medium 23 may be kept sterile for repeated deployments, without the need of any new replacement, whenever the energy transmission is completed.

The transmission medium 23 may be any material suitable for transmission of energy. Good examples include metal, plastic, organic polymers, quartz or silica glass, carbon or graphite, semi-conductors, or a combination thereof. In the preferred embodiments of the invention, the transmission medium 23 is made of optical fiber, especially an optical fiber with small diameters. Material for the cylindrical tube 10 and/or branch is not limited, while plastic or resin material is preferred, due to its low costs and processing easiness. The material of the cylindrical tube 10 may be the same as or different from that of the branch 13. Material for the telescopic arrangement 20 is not limited, while metal, plastic or resin material is preferred, considering the low costs and processing easiness. Among them, metal, especially stainless steel is preferred, due to its medical biocompatibility.

In the following, exemplary applications of the invented connector for deploying a transmission medium will be described.

In the initial state, the telescopic arrangement 20 is fully extended. That is, the first end 211 of the fixed tube 21 engages the second end 222 of the sliding tube 22. This status is referred to as a standby status. In another embodiment of the invention, in the standby status the second end 222 of the sliding tube 22 may even extend a predetermined length towards the second end 212 of the fixed tube, or extend to reach the edge of the second end 212. When the deployment is initialized, the exposed segment of the transmission medium 23 out of the second end 222 of the sliding tube 22 will be well protected by the fixed tube 21. The at least one transmission medium 23, such as an optical fiber, forms a thread shape laid in the lumen of the sliding tube 22. The tail end 232 of the transmission medium 23 is affixed to the first end 221 of the sliding tube 22 and extends out of the first end 221, where it couples with the coupler 24 immediately at the exit of the sliding tube 22 or a segment away from the exit. The coupler 24 in turn couples an energy source 25. On the other hand, the front end 231 of the transmission medium 23 extends towards the fixed tube 21, with an extension length determined by the desired depth of a location in a living organism, human body, a pouch for biological fluids or an external body fluid circulation circuit, to which the front end 231 shall reach.

When used, the second end 12 of the cylindrical tube 10 is first inserted/fit in the hub 141 of an indwelling needle 14 or catheter. The second end 12 of the cylindrical tube 10 may be a male Luer slip connector for example. In another embodiment of the invention, the second end 12 is configured to embed and couple with the hub 141 of the indwelling needle 14 or the catheter. In such an embodiment, the second end 12 of the cylindrical tube 10 may be a male Luer lock connector for example.

In the standby status, the front portion of the second end 12 enters into the space defined by the hub 141 of the indwelling needle 14 or catheter, whereby the second end 212 of the fixed tube 21 abuts the entrance of the needle 16 affixed in the hub 141 of the indwelling needle 14. At this position, the opening of the second end 212 of the fixed tube 21 will be forced to align to the entrance of the needle lumen. With such an arrangement, the connector for deploying a transmission medium aligns the front end 231 of the transmission medium 23 to the entrance of the lumen of the indwelling needle 14 or catheter, whereby the front end 231 of the transmission medium 23 may be easily and correctly deployed into the lumen of the indwelling needle 14 or catheter. FIG. 3 shows the connector for deploying an energy transmission medium in the standby status, wherein the connector is coupled into the indwelling needle 16 but the transmission medium 23 is ready for immediate deployment.

FIG. 3 shows an application in which the invented connector is used to deploy the transmission medium 23 into the indwelling needle 16. It is appreciated that the indwelling needle 16 as shown may be inserted into a body fluid container, such as a blood bag, or a connector for an extracorporeal body fluid circulation circuit, such as a hemodialysis circulation circuit, to introduce the transmission medium 23 into the body fluid container or circulation circuit.

Figure 4:
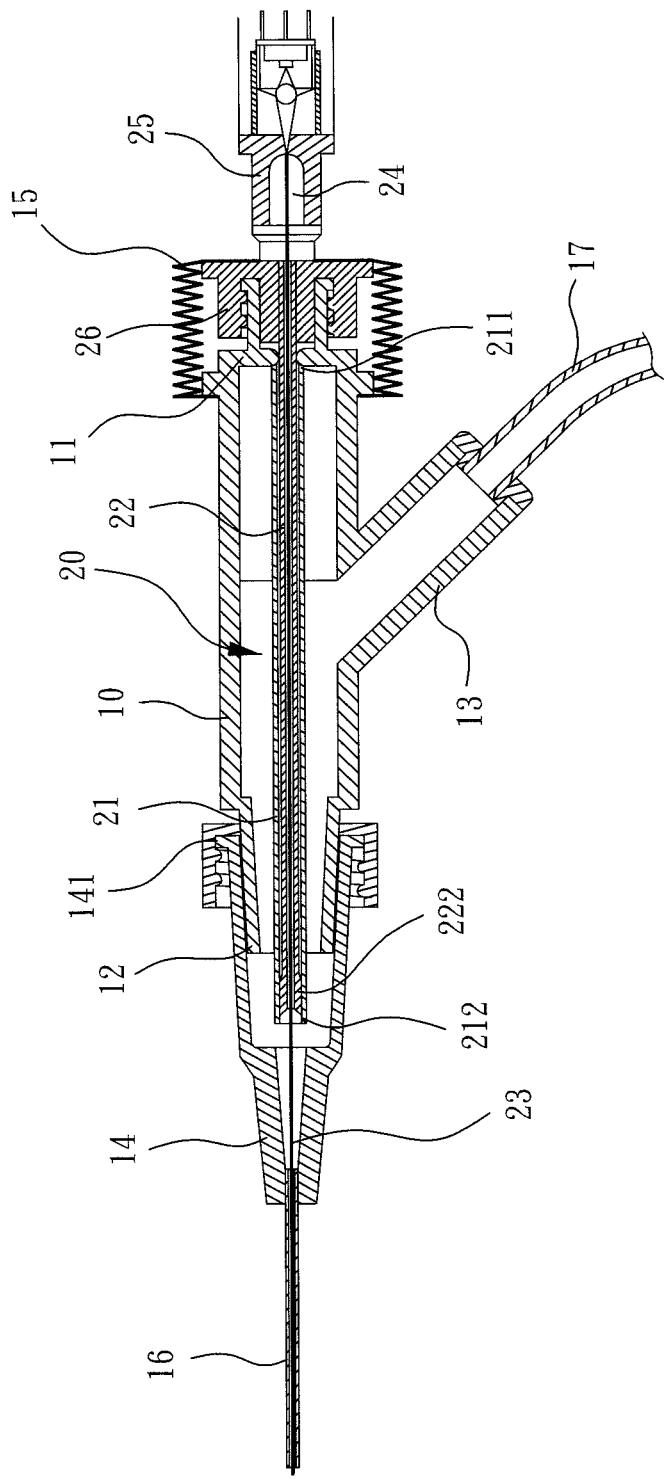
FIG. 4 shows the connector for deploying an energy transmission medium of this invention after deployment of the transmission medium.

As shown in FIG. 1, an annular lock 26 is attached at the tail end of the sliding tube 22. The annular lock 26 may be a male Luer plug. The transmission medium 23 is fixed in the sliding tube 22 by the annular lock 26. By pushing the sliding tube 22 towards the indwelling needle 14 or catheter, the sliding tube 22 will merge into the fixed tube 21, therefore moves the transmission medium 23, such that the front end 231 of the transmission medium 23 protrudes from the opening of the second end 212 of the fixed tube 21. As the front end 231 of the transmission medium 23 is already in alignment with the entrance of the lumen of the indwelling needle 14, it continues to move into the lumen cavity of the needle 14. Continue to push the telescopic arrangement 20 until the front end 231 of the transmission medium 23 reaches the desired depth in the living organism. FIG. 4 shows the status of this invention after the deployment of an energy transmission medium is complete.

In some embodiments of the invention, when the sliding tube 22 is fully plunged into the fixed tube 21, the annular lock 26 at the first end 221 of the sliding tube 22 abuts and is locked on the first end 11 of the cylindrical tube 10, so that the telescopic arrangement 20 is hold on the status of fully retraction. In other embodiments of this invention, the tail end 232 of the transmission medium 23 protrudes from the first end 221 and is coupled by the coupler 24 at a distance away from the first end 211. In this instance, the annular lock 26 does not connect the coupler 24 directly.

After the energy transmission is completed, the annular lock 26 unlocked, then the sliding tube 22 pulled back, the telescopic arrangement 20 extended and the transmission medium 23 is withdrawn back to the fixed tube 21 from the lumen of the needle 16. The connector returns to its standby status. According to this invention, as long as the sliding tube 22 is plunged the transmission medium 23 will be introduced into the lumen of the needle 16 again and reach the desired depth in the living organism. Of course, it is also possible to leave the transmission medium 23 in situ, after the transmission is completed, because the diameter of the transmission medium 23 is far smaller than the caliber of the needle lumen; the transmission medium 23 won't hinder fluids, such as injection fluids or body fluids from flowing through the lumen of the needle 16.

If the cylindrical tube 10 provides a branch 13, a catheter 17 may be coupled with the branch 13, either to introduce fluids, such as injection fluids into the indwelling needle 14, or to draw fluids, such as body fluids from the indwelling needle 14, both via the catheter 17.

Figure 5:
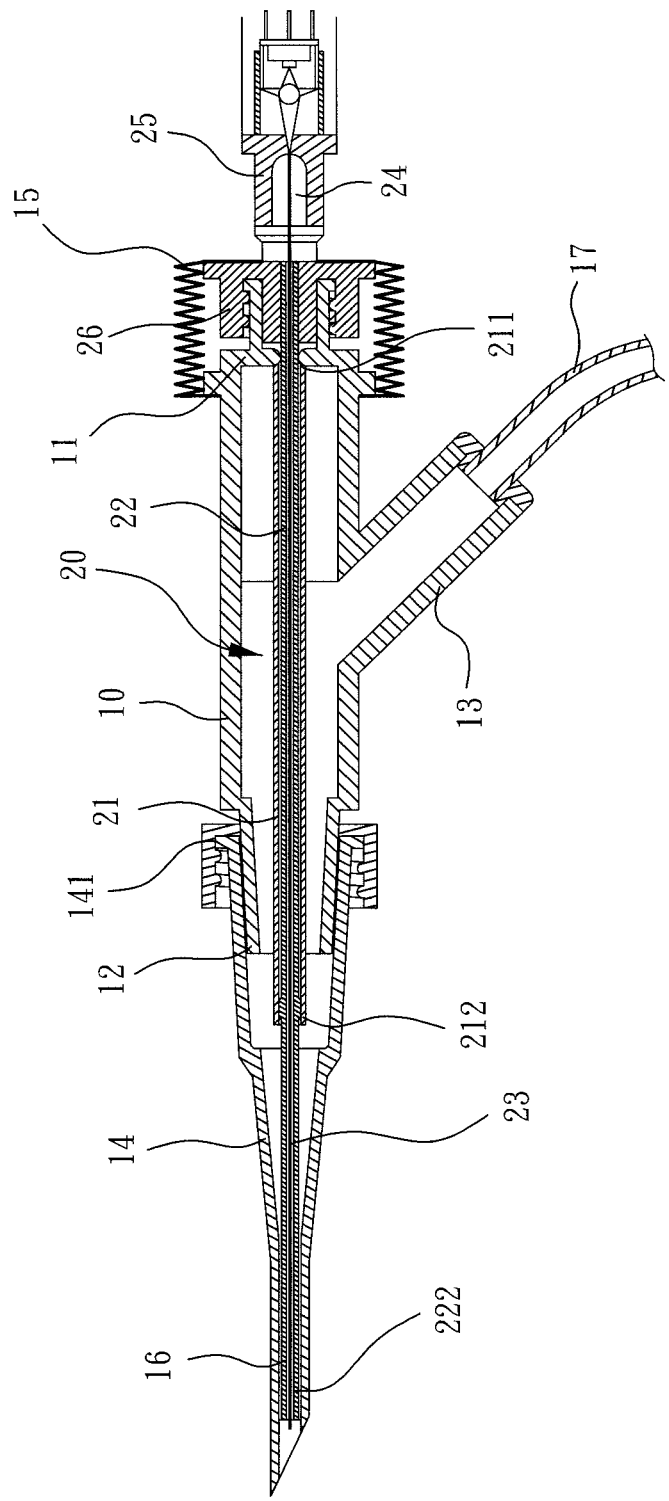
FIG. 5 shows the structural schematics of another embodiment of the connector for deploying an energy transmission medium of this invention.

FIG. 5 shows the structural schematics of another embodiment of the connector for deploying an energy transmission medium of this invention. Elements that are the same or similar to those in FIG. 1 are labelled with the same reference numbers. In the embodiment shown in FIG. 5, the second end 222 of the sliding tube 22 of the telescopic arrangement 20 extends to reach the second end 212 of the fixed tube 21, therefore, when the telescopic arrangement 20 retracts, i.e., when the sliding tube 22 slides towards the second end 212 of the fixed tube 21, the second end 222 of the sliding tube 22 moves along with the front end 231 of the transmission medium 23. In the application shown in FIG. 5, the indwelling needle 14 would be a large caliber injection syringe, such as a B.I.G. bone injection gun (PerSysMedical) or other intraosseous infusion devices. The needle 16 has an inner diameter large enough to accommodate the sliding tube 22. In this instance, the sliding tube 22 and the transmission medium 23 together can reach the location deep in the living organism penetrated by the needle 16.

The foregoing is a description of several embodiments of the connector for deploying a transmission medium, in particular optical fiber of the present invention. It will be appreciated by those having ordinary skilled in the art that embodiments of the present invention may be modified with known techniques to achieve the same or similar effects. Therefore, these modifications are within the scope of the present invention.

What is claimed is:

1. A connector for deploying an energy transmission medium, comprising:
    a cylindrical tube comprising a first end and a second end, wherein the first end is sealed; and
    a telescopic arrangement comprising a fixed tube comprising a first end and a second end, wherein the first end is attached to and penetrating the sealed first end of the cylindrical tube, extending along a longitudinal direction of the cylindrical tube and having a maximum outer diameter smaller than an inner diameter of the cylindrical tube, leaving a tunnel connecting an inner space of the cylindrical tube and the environment, and a sliding tube slidably engaged with the fixed tube and comprising a first end and a second end, wherein an orientation of the first end to the second end of the fixed tube is identical to an orientation of the first end to the second end of the cylindrical tube;
    wherein at least one energy transmission medium is attached to the sliding tube, with a front end of the transmission medium extending through out of the sliding tube towards the second end of the cylindrical tube and a tail end of the transmission medium extended from the first end of the sliding tube and coupled by a coupler to couple the tail end of the transmission medium to an energy source.

2. The connector for deploying a transmission medium according to claim 1, wherein the cylindrical tube further comprises a branch and wherein an inner cavity of the branch is in connection with an inner cavity of the cylindrical tube.

3. The connector for deploying a transmission medium according to claim 2, wherein the branch and a main body of the cylindrical tube form an angle at their joint.

4. The connector for deploying a transmission medium according to claim 1, wherein the transmission medium comprises at least one optical fiber.

5. The connector for deploying a transmission medium according to claim 1, wherein the transmission medium comprises at least one metal wire.

6. The connector for deploying a transmission medium according to claim 1, wherein the front end of the transmission medium extends to the second end of the fixed tube.

7. The connector for deploying a transmission medium according to claim 1, wherein the transmission medium is coupled by the coupler at a position immediate to the first end of the sliding tube.

8. The connector for deploying a transmission medium according to claim 1, wherein the transmission medium is coupled by the coupler at a distance from the first end of the sliding tube.

9. The connector for deploying a transmission medium according to claim 1, wherein a male Luer plug is provided to encapsulate the first end of the sliding tube and the coupler is attached to the male Luer plug.

10. The connector for deploying a transmission medium according to claim 1, wherein the sliding tube further extends towards the second end of the fixed tube for a length.

11. The connector for deploying a transmission medium according to claim 1, wherein the telescopic arrangement comprises linear sleeve tubes.

12. The connector for deploying a transmission medium according to claim 1, wherein the telescopic arrangement comprises sleeve tubes in arc shapes.

13. The connector for deploying a transmission medium according to claim 1, wherein in the telescopic arrangement a tube with a largest outer diameter extends to reach a position adjacent to the open second end of the cylindrical tube.

14. The connector for deploying a transmission medium according to claim 1, wherein in the telescopic arrangement a tube with a largest outer diameter extends beyond the second end of the cylindrical tube.

15. The connector for deploying a transmission medium according to claim 1, wherein the second end of the cylindrical tube has a decreased outer diameter and is configured to be coupled into a hub of an indwelling needle or a catheter.

16. The connector for deploying a transmission medium according to claim 1, wherein the second end of the cylindrical tube is configured to couple a hub of an indwelling needle or a catheter by encapsulating the hub.

17. The connector for deploying a transmission medium according to claim 1, further comprising a flexible tube bag connecting the coupler of the sliding tube and the first end of the cylindrical tube and enclosing a space between the coupler and the first end of the cylindrical tube.

18. The connector for deploying a transmission medium according to claim 1, further comprising a fixer provided in at least one of the fixed tube and the sliding tube, to fix the relative positions of the two tubes, after they are engaged.

19. The connector for deploying a transmission medium according to claim 1, further comprising a stopper provided in at least one of the fixed tube and the sliding tube, to prevent the two tubes from separation when the telescopic arrangement is fully extended or fully retracted, after the two tubes are engaged.

* * * * *